(12) United States Patent
Tremont

(10) Patent No.: US 6,890,524 B1
(45) Date of Patent: *May 10, 2005

(54) HYDROLYZABLE DELIVERY SYSTEM USING CROSS-LINKED POLYMERIC RESINS AS VEHICLES

(75) Inventor: Samuel J. Tremont, Manchester, MO (US)

(73) Assignee: Monsanto Company, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/647,503

(22) PCT Filed: Mar. 30, 1998

(86) PCT No.: PCT/US98/06144

§ 371 (c)(1), (2), (4) Date: Feb. 21, 2001

(87) PCT Pub. No.: WO98/44951

PCT Pub. Date: Oct. 15, 1998

Related U.S. Application Data
(60) Provisional application No. 60/042,641, filed on Apr. 4, 1997.

(51) Int. Cl.$^7$ ............................................. A61K 31/75
(52) U.S. Cl. ..................... 424/78.18; 514/690; 525/46; 525/169; 525/218; 525/255; 525/259; 525/330.5; 525/330.4; 525/333.3; 525/340
(58) Field of Search .......................... 424/78.18, 78.17, 424/499, 422, 179, 78.27; 514/690; 525/46, 169, 218, 255, 259, 340, 330.5, 330.4, 333.3, 102, 355, 332.7, 332.8, 332.9, 333.1, 341, 379, 331.2

(56) References Cited

U.S. PATENT DOCUMENTS

| | | | |
|---|---|---|---|
| 4,228,152 A | 10/1980 | Ferruti et al. .................. | 424/81 |
| 4,615,697 A | 10/1986 | Robinson ..................... | 604/890 |
| 4,663,308 A | 5/1987 | Saffran et al. .................. | 514/3 |
| 4,921,707 A | 5/1990 | Racz et al. .................. | 424/690 |
| 5,169,640 A | 12/1992 | France et al. ................ | 424/470 |
| 5,275,824 A | 1/1994 | Carli et al. .................. | 424/490 |
| 5,474,767 A | 12/1995 | Tremont .................. | 424/78.27 |
| 5,607,691 A * | 3/1997 | Hale et al. .................... | 424/449 |
| 5,783,214 A * | 7/1998 | Royer ......................... | 424/422 |
| 5,827,925 A * | 10/1998 | Tremont et al. .......... | 424/78.17 |
| 6,096,834 A * | 8/2000 | Tremont ..................... | 424/449 |
| 6,471,955 B1 * | 10/2002 | Tremont et al. .......... | 424/78.18 |

FOREIGN PATENT DOCUMENTS

| | | | |
|---|---|---|---|
| WO | 92/01477 | 2/1992 | .......... A61K/47/48 |
| WO | 95/28916 | 11/1995 | ............ A61K/9/16 |

OTHER PUBLICATIONS

Ebert et. al. (Journal of Biomedical materials Research, vol. 16, 629–638, 1982.*
Blossey et. al (J. Org Chemistry, 1990, 55,4664–4668).*
Sarobe et. al. (Polymers for Advanced Technologies, vol. 7, 749–753, 1996).*
Severian et al Reaserch Paper "Bioactive Polymers" 58 Chim OGGI, Sep. 1988, No. 9, 59–63).*
J. Kopecek, et al., "Polymers for colon–specific drug delivery", Journal of Controlled R I ase, vol. 19, Nos. 1–3 (1992), pp. 121–130.
S. Tremont, et al., "Catalytic Functionalization of Polymers: A Novel Approach to Site Specific Delivery of Misoprostol to the Stomach", Journal of Medicinal Chemistry, vol. 36, No. 21 (1993), pp. 3087–3097.
P. Yeh, et al., "Site–specific drug delivery and penetration enhancement in the gastroint stinal tract", Journal of Controlled Release, vol 36, (1995), pp. 109–124.
A. Bilia, et al., "In vitro evaluation of a pH–sensitive hydrogel for control of GI drug delivery from silicone–based matrices", International Journal of Pharmaceutics, vol. 130, (1996), pp. 83–92.
I. Kim, et al., "Drug Release from pH–sensitive Interpenetrating Polymer Networks Hydrogel Based on Poly (ethylene glycol) Macromer and Poly (acrylic acid) Prepared by UV Cured Method", Archives of Pharmacal Research, vol. 19, No. 1 (1996), pp. 18–22.
P.A. Parsons–Wingerter, "Cooperativity in Hepatocyte Culture from Cell–Cell and Cell–Substrat Interactions", Dissertation Abstracts International, vol. 54, No. 1, (1993) p. 368.
C, Larsen et al., "Macromolecular Prodrugs", Acta Pharm. Suec., vol. 25, No. 1, (1988) pp. 1–14.
E. Teslariu et al., "The Investigations on Some Pharmacokinetic Properties of Metronidazol Bound on Polymeric Support", Biopharm. Pharm. Technol., $1^{st}$, (May 1995) pp. 903–904.

* cited by examiner

Primary Examiner—Tatyana Zalukaeva
(74) Attorney, Agent, or Firm—Eric J. Baude; Karen B. King

(57) ABSTRACT

This invention provides a method of preparing a polymeric delivery system for active ingredients. The delivery system is formed either by attaching the active ingredient to a linker through a hydrolyzable covalent bond, then forming a covalent bond between the linker and a portion of the subunits of a cross-linked polymer, or by attaching a linker to a portion of the subunits of a cross-linked polymer, then attaching the active ingredient to the polymer-linker combination through a hydrolyzable covalent bond. The invention also provides a delivery system comprising an active ingredient covalently bonded through a hydrolyzale covalent bond to a linker, which is in turn covalently bonded to a portion of subunits of a cross-linked polymer.

6 Claims, No Drawings

HYDROLYZABLE DELIVERY SYSTEM USING CROSS-LINKED POLYMERIC RESINS AS VEHICLES

This application claims the benefit of U.S. Provisional Application No. 60/042,641, filed Apr. 4, 1997.

BACKGROUND OF THE INVENTION

1. Field of the Invention

This invention relates to a delivery system comprising an active ingredient covalently bonded to a linker by formation of an ester, carboxylic acid anhydride, amide, thioester, or enol ester, which is in turn covalently bonded to a portion of subunits of a crosslinked polymer. The invention also relates to a method for preparing the hydrolyzable delivery system.

2. Related Background Art

Polymeric materials are frequently used to achieve controlled oral delivery of drugs. In most controlled-release devices, the drug molecule is not covalently bonded to the polymer, which acts merely as a barrier or as a reservoir from which the drug diffuses. The diffusion is often controlled by the degree of swelling of the polymer matrix on contact with aqueous media, as in the systems described in U.S. Pat. Nos. 5,275,824; 5,169,640; 4,921,707; 4,615,697; and in PCT Application Wo 95/28916. However, some controlled-release systems are pH-selective, allowing release of the drug only within a specified pH range.

An example of pH-selective delivery can be found in polymeric systems consisting of interpenetrating networks of polyethylene glycol and polyacrylic acid. Such systems are disclosed in the International Journal of Pharmacy, Vol. 130, page 83 (1996) and in Archives of Pharmacal Research, Vol. 19, page 18 (1996). The polymeric network of these systems does not swell at gastric pH, but does swell on contact with the higher pH of the intestines, allowing release of the drug in the intestines. The swelling is believed to be due to deprotonation of the acrylic acid functional groups at the higher pH.

A delivery system to accomplish selective delivery to a particular site in the body is described in U.S. Pat. No. 4,663,308. In this system, a polymer which is crosslinked with a compound containing azo bonds is used as a coating for the drug substance. These azo bonds are reduced by enzymes in the large intestine, leading to cleavage of the crosslinks, causing the polymer coating to disintegrate, thereby releasing the drug in the large intestine.

Systems similar to the one described in U.S. Pat. No. 4,663,308 are described in the Journal of Controlled Release: Vol. 19, page 121 (1992); and Vol. 36, page 109 (1995). The polymers employed in these systems do not swell at the typical gastric pH value of from 1 to 4, but pass unchanged into the intestine, where the higher pH value causes the polymer matrix to swell. The swelling allows enzymes in the intestine to enter the polymer and break the azo crosslinks in the polymer matrix, which in turn allows the drug to diffuse through the uncrosslinked polymer matrix.

None of the aforementioned controlled-release systems contains a drug which is covalently bonded to the polymer matrix. U.S. Pat. No. 4,228,152 describes a prostaglandin delivery system in which the prostaglandin molecule is covalently bonded to a polyacrylate or polymethacrylate chain directly, or indirectly through an oxyalkylenic, aminoalkylenic, or oxyaminoalkylenic chain. Release of the prostaglandin is effected by the gradual hydrolysis of the bonds connecting the prostaglandin to the polymer matrix.

A delivery system in which a covalently-bonded drug is selectively released at a predetermined pH is described in PCT Application No. WO 92/01477; U.S. Pat. No. 5,474,767; and Journal of Medicinal Chemistry, Vol. 36, p. 3087 (1993). In these references, pH-selective drug delivery systems comprise a drug covalently bonded to a linker by reaction with a silyl chloride functional group on the linker, thus forming an acid-sensitive silyl ether bond, and a polymer which is covalently bonded to the linker-drug combination. The polymer is crosslinked following bonding of the linker, or in some cases, prior to bonding of the linker. The exemplified preferred polymer in the inventions of WO 92/01477 and U.S. Pat. No. 5,474,767 is a polybutadiene containing amine functional groups. The invention of U.S. Pat. No. 5,474,767 is limited to polymers derived from non-aromatic unsaturated monomers. Other suitable polymers described in WO 92/01477 are polyamines, polybutadienes, copolymers of 1,3-dienes, polysaccharides, hydroxypropylmethylcellulose, amino-celluloses and proteins, e.g., chitosan, and polymers of acrylic and methacrylic acids, maleic copolymers thereof, and polymers having derivatizable olefinic bonds. While the pH-sensitive site-specific delivery systems of these references provide an excellent means of rapid gastric drug delivery, polymeric site-specific delivery systems having different drug release performance characteristics would be highly advantageous.

SUMMARY OF THE INVENTION

This invention provides a method of preparing a selectively hydrolyzable polymeric delivery system for an active ingredient. The delivery system is formed either by attaching the active ingredient to a linker through a hydrolyzable covalent bond formed between a hydroxyl, $CO_2H$, amino, mercapto, or enolizable carbonyl substituent on the active ingredient and a reactive group on the linker to form an ester, carboxylic acid anhydride, amide, thioester, or enol ester, and then attaching the active ingredient-linker combination to a portion of the subunits of a crosslinked polymer through a linker-polymer covalent bond formed between the linker and a reactive group on the polymer, or by attaching a linker to the polymer and then attaching the active ingredient to the polymer-linker combination. The invention also provides a delivery system comprising an active ingredient covalently bonded through a hydrolyzable covalent bond to a linker which is in turn covalently bonded to a portion of subunits of a crosslinked polymer.

DETAILED DESCRIPTION OF THE INVENTION

The following terms used herein are defined. The term "THF" indicates the solvent tetrahydrofuran. The term "DMF" indicates the solvent N,N-dimethylformamide. The term "mercapto" refers to the substituent moiety SH, bonded through its sulfur atom to a carbon atom on a substrate. The term "alkyl", refers to a straight or branched alkyl group containing from 1 to 20 carbon atoms. The term "alkenyl" refers to a straight or branched hydrocarbon group containing from 1 to 20 carbon atoms and at least one carbon—carbon double bond. The term "alkynyl" refers to a straight or branched hydrocarbon group containing from 1 to 20 carbon atoms and at least one carbon—carbon triple bond. The term "cycloalkyl" refers to a cyclic alkyl group containing up to 20 carbon atoms. The term "alkanoyl" refers to a group formed by an alkyl group bonded to a carbonyl group. The term "aryl" refers to a group derived from a cyclic aromatic compound having up to 20 carbon atoms.

The term "aroyl" refers to a group formed by an aryl group bonded to a carbonyl group. The term "aralkyl" refers to an alkyl substituent substituted by an aryl group. The term "alkaryl" refers to an aryl substituent substituted by an alkyl group. The term "derivatized carboxylic acid substituent" refers to a carbonyl group attached to a leaving group, including, but not limited to: hydroxy, halo, alkoxy, aryloxy, alkanoyloxy, aroyloxy, aryloxy substituted by electron-withdrawing groups, and quaternary amines. The term "halo" means a fluoro, chloro, bromo, or iodo group. The term "subunit" refers to a portion of a polymer chain derived from a single molecule of monomer; subunits are often referred to in the art as "repeat units". A "styrenic" subunit is one derived from a monoethylenically unsaturated styrene monomer. Each type of subunit is repeated in the polymeric system depending on the initial composition of monomers used to produce the polymer.

In the delivery system of this invention, the active ingredient is covalently bonded through a hydrolyzable covalent bond to a linker, which is in turn covalently bonded to a crosslinked polymeric resin. Attachment of the active ingredient by means of covalent bonds prevents release of active ingredient until conditions occur which will break the covalent bonds, and prevents continued release after these conditions cease to exist. Such conditions for release by the cleavage of the hydrolyzable covalent bond formed with the linker will be dependent on the condition of the medium into which the delivery system is introduced, e.g. pH or enzymatic content.

The delivery system of this invention is based on a crosslinked polymeric material. Suitable polymeric materials include polystyrenes, polyamines, polybutadienes, copolymers of 1,3-dienes, polysaccharides, hydroxypropylmethylcellulose, and polymers of acrylic and methacrylic acid including copolymers thereof, maleic copolymers, and any polymer having derivatizable olefinic bonds. The term "copolymer" is used herein to mean polymers which are produced from more than one monomer. Preferred polymers useful in this invention may be selected from the group consisting of poly[(4-halomethyl)styrene], poly[(3-halomethyl)styrene], mixtures of poly[(4-halomethyl)styrene] and poly[(3-halomethyl)styrene], poly[(4-dialkylaminomethyl)styrene], poly[(3-dialkylaminomethyl)styrene], and mixtures of poly[(4-dialkylaminomethyl)styrene] and poly[(3-dialkylaminomethyl)styrene]. The styrene subunits of the preferred polystyrene polymers employed in this invention have a reactive group R substituted at the 3 or 4 position of the styrene aromatic ring. The R group is capable of forming a covalent bond by reaction with a reactive group on a linker. Particularly preferred R groups are dialkylaminomethyl groups or halomethyl groups, most preferably substituted at the 4 position of the styrene. The most preferred polymers are poly[(4-chloromethyl)styrene], poly[(3-chloromethyl)styrene], mixtures of poly[(4-chloromethyl)styrene] and poly[(3-chloromethyl)styrene], poly[(4-dimethylaminomethyl)styrene], poly[(3-dimethylaminomethyl)styrene], and mixtures of poly[(4-dimethylaminomethyl)styrene] and poly[(3-dimethylaminomethyl)styrene]. The preferred polymers are well known or may readily be prepared without undue experimentation. For example, in one procedure, they may be synthesized from a mixture of monomers containing the appropriate substituted styrene, preferably a 4-substituted styrene, and an amount of divinylbenzene suitable to produce the desired amount of crosslinking. Preferably, divinylbenzene is present in an amount ranging from 0.5% to 4% by weight, based on the total weight of monomers. Most preferably, the amount of divinylbenzene is about 2% by weight, based on the total weight of monomers. Another procedure for synthesizing poly[(4-chloromethyl)styrene], poly[(3-chloromethyl)styrene], or mixtures thereof, is to react a styrene-divinylbenzene copolymer with a chloromethylating complex according to the procedure described in European Patent Application 277,795, the disclosure of which is incorporated by reference herein.

When the polymer is a poly(haloalkyl substituted styrene), e.g., poly[(4-chloromethyl)styrene] or poly[(3-chloromethyl)styrene], a linker is used which contains a dialkylamino group which reacts with a portion of the haloalkyl groups, e.g., a 4-chloromethyl or 3-chloromethyl group, present on most of the polymer subunits to form a quaternary ammonium salt. The most preferred polymers if the linker contains a dialkylamino group are poly[(4-chloromethyl)styrene] and poly[(3-chloromethyl)styrene]. When the polymer is dialkylamino-substituted, e.g., poly[(4-dialkylaminomethyl)styrene] or poly[(3-dialkylaminomethyl)styrene], a linker is used which contains a haloalkyl group, e.g., a chloromethyl group, which reacts with a portion of the dialkylamino groups, e.g., 4-dialkylaminomethyl or 3-dialkylaminomethyl group, present on most of the polymer subunits to form a quaternary ammonium salt. The most preferred polymers if the linker contains a chloromethyl group are poly[(4-dimethylaminomethyl)styrene] and poly[(3-dimethylaminomethyl)styrene].

The linker is a molecule with reactive substituents allowing it to be covalently bonded to both the active ingredient and the crosslinked polymeric resin in such a way that a hydrolyzable compound is produced which will undergo cleavage under a variety of conditions to release the active ingredient. The substituent which reacts with a functional group on the active ingredient forms an ester, carboxylic acid anhydride, amide, thioester, or enol ester, all of which are susceptible to hydrolysis at varying rates depending on which of these compounds is formed and the substituents thereon. The reactive substituent on the linker that reacts with the crosslinked polymer to covalently bond the linker to the polymer is any substituent which will form a nitrogen-carbon, oxygen-carbon, sulfur-carbon, or phosphorus-carbon bond with a polymer subunit, preferably a halo or dialkylamino substituent. Preferably, the linker is a compound having a hydroxyl or a derivatized carboxylic acid substituent at one end of the molecule and a halo or dialkylamino substituent at the other end. The preferred linker has the structure

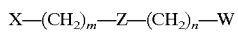

X—(CH$_2$)$_m$—Z—(CH$_2$)$_n$—W wherein X is halo or dialkylamino: W is OH or COY, wherein Y is halo, hydroxy, alkoxy, aryloxy, aryloxy substituted by an electron-withdrawing group, alkanoyloxy, or aroyloxy; m is an integer from 0 to 2, inclusive; n is an integer from 0 to 2, inclusive; and Z is a divalent aryl, cycloalkyl, alkyl, alkenyl, or alkynyl group. The derivatized carboxylic acid substituent, —COY, reacts with a hydroxyl, CO$_2$H, amino, mercapto, or enolizable carbonyl substituent on the active ingredient, forming an ester, carboxylic acid anhydride, amide, thioester, or enol ester respectively. When W is OH, the hydroxyl substituent reacts with a CO$_2$H substituent on the active ingredient forming an ester.

Most preferably, the linker is a compound having the following structure:

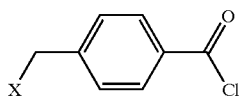

When X is a halo substituent, the linker forms a covalent bond with a dialkylamino-substituted polymer, e.g., poly[(4-dialkylaminomethyl)styrene] or poly[(3-dialkylaminomethyl)styrene], by alkylating the dialkylamino group to produce a quaternary ammonium salt. In this case, an alkyl halide is then optionally added to produce a quaternary ammonium salt at each unreacted dialkylamino substituent. In another embodiment, the polymer is treated first with an amount of alkyl halide sufficient to produce a quaternary ammonium salt on only a portion of the dialkylamino substituents, and then the linker is attached to substantially all of the remaining dialkylamino-substituents. When X is a dialkylamino substituent, the linker forms a covalent bond with a halomethyl substituted polymer, e.g., poly[(4-chloromethyl)styrene] or poly[(3-chloromethyl)styrene], which alkylates the dialkylamino substituent to produce a quaternary ammonium salt. In this case, a trialkylamine is optionally added to produce a quaternary ammonium salt at each unreacted haloalkyl substituent. In another embodiment, the polymer is treated first with an amount of trialkylamine sufficient to produce a quaternary ammonium salt on only a portion of the haloalkyl substituents, and then the linker is attached to substantially all of the remaining haloalkyl substituents.

The active ingredient in this invention may be any substance that is desired for administration by selective hydrolytic release, such as a drug, a seqeustrant, or a ligand for complexation of metals. In each case, a suitable active ingredient will be one which forms a hydrolyzable covalent bond with a reactive group on the linker. The active ingredient may be substituted by a hydroxyl, $CO_2H$, amino, mercapto, or enolizable carbonyl substituent group which is capable of reacting with a reactive group on the linker to form a covalent bond. Preferably, the active ingredient is a biologically active material, e.g., a drug, intended to be administered orally, especially those wherein controlled release in the gastrointestinal system is preferred, or wherein control of the rate of release is desired for systemic action. For example, drugs for which delivery to the stomach is preferred include natural or synthetic prostaglandins and prostacyclins (e.g., misoprostol, enisoprost, enprostil, iloprost, and arbaprostil), any other drugs for treatment or prevention of peptic ulcers, gastric antisecretory drugs, antimicrobial drugs, prokinetic drugs, cytoprotective drugs and the like. Preferred prostaglandin drugs which may be delivered by the delivery system of this invention are those described in PCT Application No. WO 92/01477, the specification of which is incorporated herein. Exemplary antimicrobial drugs include tetracycline, metronidazole and erythromycin which can be used for the eradication of gastric microbes. Other suitable drugs for administration to the gastrointestinal tract include the non-steroidal antiinflammatory drugs, including, for example, p-aminosalicylic acid, ibuprofen, ketoprofen, and flurbiprofen. The drug delivery system of this invention may be used to deliver more than one drug at a time, if there is a therapeutic need for simultaneous release of multiple drugs. The amount of the active ingredient incorporated into the polymer depends on the desired amount of the particular active ingredient to be delivered. In general the amount of active ingredient is in the range from about 0.03% by weight to about 50% by weight of the polymeric delivery system, preferably in the range from about 0.05% by weight to about 20% by weight of the polymeric delivery system, and most preferably from 0.05% by weight to 2% by weight of the polymeric delivery system.

The preferred amount of delivery system to be administered is an amount that is sufficient to prevent, cure, or treat a condition for a desired period of time for which the delivery system of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the subject in which it is used, and the body weight of that subject. An effective amount is that amount which in a composition of this invention provides a sufficient amount of the active ingredient to provide the requisite activity of the active ingredient in the body of the treated subject for the desired period of time, and can be less than that amount usually used.

Inasmuch as amounts of particular active ingredients that are suitable for treating particular conditions are generally known, it is relatively easy to formulate a series of delivery systems containing a range of such active ingredients to determine the effective amount of such an active ingredient for a particular delivery system. Based upon a reading of the description herein and of the following examples, it is within the skill of the art to select an amount of any particular active ingredient and to covalently bond such an amount to a polymer herein described for delivering an effective amount of such an active ingredient. While the effective amount for all active ingredients cannot be stated, typical compositions of this invention may contain about one microgram to about one gram of active ingredient per dose administered. More preferably, a composition of this invention may contain about 1 microgram to about 250 milligrams per dose.

The method for preparing the delivery system of this invention comprises two steps. In one embodiment, the first step is attaching the active ingredient to a linker by forming a hydrolyzable covalent bond to produce a hydrolyzable compound of one of the aforementioned types. The linker used in this embodiment may be a commercially available material with the aforementioned reactive groups. The active ingredient-linker combination is then attached to one of the aforementioned crosslinked polymers by forming a covalent nitrogen-carbon, oxygen-carbon, sulfur-carbon, or phosphorus-carbon bond between the active ingredient-linker combination and a portion of the subunits of the polymer.

Another embodiment of the method for preparing the delivery system also comprises two steps. However, in this embodiment, the first step is attaching the linker to a portion of the subunits of one of the aforementioned crosslinked polymers to form a covalent nitrogen-carbon, oxygen-carbon, sulfur-carbon, or phosphorus-carbon bond. The linker-polymer combination is then attached to the active ingredient by forming a hydrolyzable covalent bond between the linker and the active ingredient to produce one of the aforementioned hydrolyzable compounds.

Preparation of an active ingredient-linker combination is accomplished in a preferred embodiment of this invention by coupling the active ingredient to the linker, typically by combining the drug and the most preferred linker described above, with X being a chloromethyl group. Suitable solvents for this step include those which are capable of dissolving the drug, but which are not reactive towards the acyl chloride functional group, including the halogenated solvents such as chlorobenzene, 1,2-dichlorobenzene, dichloromethane, tetrachloromethane, chloroform, 1,2-dichloroethane, 1,1,1-trichloroethane, 1,1,2,2-tetrachloroethane, and the like. Preferred solvents are dichloromethane and 1,2-dichloroethane. The most preferred solvent is dichloromethane. In addition, a base may be added to remove hydrogen chloride formed in the reaction. Preferred bases include trialkylamines. The most preferred base is triethylamine. This reaction is preferably carried out at a temperature in the range from about 15° C. to about 100° C., most preferably from 20° C. to 40° C. Preferably, the reaction is allowed to proceed for a period of about 1 to about 18 hours. The progress of the reaction may be followed by using a method capable of detecting the level of starting material, product, or both, such as thin-layer chromatography or liquid chromatography. The reaction is typically allowed to proceed until analysis indicates that the starting material is substantially consumed.

In one embodiment of the method of this invention, following the preparation of an active ingredient-linker combination, the active ingredient-linker combination is coupled to a crosslinked resin, e.g., poly[(4-dialkylaminomethyl)styrene] or poly[(3-dialkylaminomethyl)styrene] resin, to form the active ingredient delivery system. In a preferred embodiment of this invention, a crosslinked poly[(4-chloromethyl)styrene] or poly[(3-chloromethyl)styrene], or a mixture thereof is first combined with a dialkylamine in a solvent to produce a poly[(4-dialkylaminomethyl)styrene] or poly[(3-dialkylaminomethyl)styrene], or a mixture thereof. Suitable crosslinked poly[(4-chloromethyl)styrene] or poly[(3-chloromethyl)styrene] resins are commercially available resins, including those manufactured by Purolite International Limited, Mid Glamorgan, Wales. The most preferred resin is one made with a divinylbenzene monomer content of about 2% by weight. Suitable dialkylamines include dimethylamine, methylethylamine, diethylamine, methylpropylamine, methylbutylamine, methylisopropylamine, methylpropylamine, and the like. The most preferred dialkylamine is dimethylamine. Solvents which are suitable for this reaction include tetrahydrofuran (THF), ethyl acetate, dichloromethane, toluene, alcoholic solvents, and water, and mixtures thereof. The preferred solvents are THF, ethyl acetate and dichloromethane. The most preferred solvent is THF.

The delivery system is then prepared by combining the active ingredient-linker combination and the crosslinked polymeric resin in a solvent. Suitable solvents for this step include those which are polar and capable of swelling the crosslinked polymeric resin sufficiently to allow for rapid reaction with the active ingredient-linker combination. Examples of such solvents include tetrahydrofuran (THF), N,N-dimethylformamide (DMF), ethyl acetate, and dichloromethane. The most preferred solvent is THF. An iodide salt may be added to promote the reaction. Suitable iodide salts include tetrabutylammonium iodide, tetrapropylammonium iodide, tetraethylammonium iodide, tetramethylammonium iodide, potassium iodide, sodium iodide, cesium iodide, and the like. Preferred iodide salts include tetrabutylammonium iodide and potassium iodide. The most preferred salt is tetrabutylammonium iodide. This reaction is typically carried out at a temperature in the range from about 15° C. to about 100° C., most preferably from 25° C. to 40° C. Preferably, the reaction is allowed to proceed for a period of about 5 to about 18 hours. The progress of the reaction may be followed by using a method capable of detecting the level of starting material, product, or both, e.g., thin-layer or liquid chromatography. The reaction is typically allowed to proceed until the starting material is substantially consumed. After the reaction period, the resin is isolated.

The resin is preferably then reacted with an alkyl halide to alkylate substantially all of the remaining dialkylamino groups on the resin. Suitable alkyl halides for this purpose include methyl chloride, ethyl chloride, propyl chloride, isopropyl chloride, butyl chloride, and the like. The most preferred alkyl halide is methyl chloride. This reaction is typically carried out at a temperature in the range from about 10° C. to about 50° C., most preferably from about 15° C. to about 30° C. Preferably, the reaction is allowed to proceed for a period of about 1 hour to about 3 days, most preferably from 2 to 3 days.

In another embodiment of this invention, the alkyl halide is added to the crosslinked dialkylamino-substituted polymer in an amount sufficient to produce a quaternary ammonium salt at only a portion of the subunits, and then the active ingredient-linker combination is attached to the remaining dialkylamino groups.

In another preferred embodiment of this invention, the aforementioned active ingredient-linker combination, which bears a chloromethyl group is treated with a dialkylamine in a solvent to produce the active ingredient-dialkylamino-substituted linker combination. Suitable dialkylamines for this reaction include dimethylamine, methylethylamine, diethylamine, methylpropylamine, methylbutylamine, methylisopropylamine, ethylpropylamine, and the like. The most preferred dialkylamine is dimethylamine. The amine is added in an amount ranging from 1 to 30 equivalents based on the amount of active ingredient-linker combination, preferably from about 1 to about 2 equivalents. Suitable solvents for this reaction include THF, dichloromethane, ethyl acetate, 1,2-dichloroethane, toluene, xylenes, diethyl ether, N,N-dimethylformamide, N,N-dimethylacetamide, N-methylpyrrolidone, and 1,2-dimethoxyethane. The preferred solvents are THF and dichloromethane, and the most preferred solvent is THF. The reaction temperature for this step is suitably in the range from about 0° C. to about 100° C., preferably in the range from about 20° C. to about 40° C., and most preferably at about 25° C. The reaction time varies from about 3 hours to about 24 hours, depending on the identity of the amine and the solvent. This dialkylamino-substituted linker-active ingredient combination is then reacted with one of the aforementioned suitable crosslinked haloalkyl-substituted polymers, e.g., poly[(4-chloromethyl)styrene] or poly[(3-chloromethyl)styrene], to form the active ingredient delivery system. In a preferred embodiment of this invention, poly[(4-chloromethyl)styrene], poly[(3-chloromethyl)styrene], or a mixture thereof, is combined with the dialkylamino-substituted linker-active ingredient combination in a solvent. Suitable solvents for this step include those which are polar and capable of swelling the crosslinked polymeric resin sufficiently to allow for rapid reaction with the active ingredient-linker combination. Examples of such solvents include tetrahydrofuran (THF), N,N-dimethylformamide (DMF), ethyl acetate, and dichloromethane. The most preferred solvent is THF. An iodide salt may be added to promote the reaction. Suitable iodide salts include tetrabutylammonium iodide, tetrapropylammonium iodide, tetraethylammonium iodide, tetramethylammonium iodide, potassium iodide, sodium iodide, cesium iodide, and the like. Preferred iodide salts include tetrabutylammonium iodide and potassium iodide. The most preferred salt is tetrabutylammonium iodide. This reaction is typically carried out at a temperature in the range from about 15° C. to about 100° C., most preferably from 25° C. to 40° C. Preferably, the reaction is allowed to proceed for a period of about 5 to about 18 hours. The progress of the reaction may be followed by using a method capable of detecting the level of starting material, product, or both, e.g., thin-layer or liquid chromatography. The reaction is typically allowed to proceed until the starting material is substantially consumed. After the reaction period, the resin is isolated.

The resin is preferably then reacted with a trialkylamine to form a quaternary ammonium salt on substantially all of the remaining chloromethyl groups on the resin. Suitable trialkylamines for this reaction include trimethylamine, dimethylethylamine, diethylmethylamine, dimethylpropylamine, triethylamine, dimethylbutylamine, dimethylisopropylamine, diethylpropylamine, and the like. The most preferred trialkylamine is trimethylamine. This reaction is typically carried out at a temperature in the range from about 10° C. to about 50° C., most preferably from about 15° C. to about 30° C. Preferably, the reaction is allowed to proceed for a period of about 1 hour to about 3 days, most preferably from 2 to 3 days.

In another embodiment of this invention, the trialkylamine is added to the crosslinked poly(haloalkyl substituted styrene) in an amount sufficient to produce a quaternary ammonium salt at only a portion of the subunits, and then the active ingredient-linker combination is attached to the remaining haloalkyl groups.

The examples which follow are intended as an illustration of certain preferred embodiments of the invention, and no limitation of the invention is implied.

EXAMPLE 1

Preparation of Crosslinked Poly[(4-dimethylaminomethyl)styrene]

Purolite resin D-3196 AGD:16:44 (50 g, Purolite International Limited, Mid Glamorgan, Wales), a crosslinked poly[(4-chloromethyl)styrene], was stirred for about 30 minutes in each of the following solutions, then filtered to remove the solution: deionized water (500 ml), 10% HCl solution (500 ml), deionized water (500 ml), THF (HPLC grade, two 500 ml portions), THF (anhydrous, inhibitor-free, two 500 ml portions). The resin was then extracted for 72 hours with anhydrous, inhibitor-free THF (1200 ml) in a soxhlet apparatus. The cleaned resin was dried overnight under high vacuum, and was then combined with a solution of dimethylamine in THF (2M solution, 103 g, 7 eq) and allowed to react overnight at room temperature, and then overnight at reflux. The product resin is cleaned by stirring for about 30 minutes in each of the following solutions, followed by filtration to remove the solution: THF (HPLC grade, 500 ml), deionized water (four 1 liter portions), THF (HPLC grade, 500 ml), THF (HPLC grade, two 1 liter portions), THF (anhydrous, inhibitor-free, two 1 liter portions). The resin was then dried overnight at room temperature followed by drying overnight over $P_2O_5$ at 75° C.

EXAMPLE 2

Preparation of Metronidazole-Linker Combination

Into a round-bottom flask is placed metronidazole (1.0 g, 5.8 mmol), triethylamine (0.5 ml), and dichloromethane (20 ml). A solution of 4-(chloromethyl)benzoyl chloride (Aldrich Chemical Co., Milwaukee, Wis., 1.096, 5.8 mmol) in dichloromethane (5 ml) is added at room temperature. The reaction mixture is stirred at room temperature for 24 hours. The mixture is extracted with water, and the organic layer dried with magnesium sulfate. The product is isolated by removing the solvent.

EXAMPLE 3

Preparation of Metronidazole Delivery System

The metronidazole-linker combination is combined with the resin product of Example 1 and tetrabutylammonium iodide in THF and maintained at 40° C. for 72 hours. After washing the resin with THF, methyl chloride (20% by volume in THF) is added and allowed to react at room temperature for 64 hours. After filtration to remove solvent, the product is obtained.

Other variations and modifications of this invention will be obvious to those skilled in the art. This invention is not limited except as set forth in the claims.

What is claimed is:

1. A delivery system comprising: an active ingredient covalently bonded to a linker through a hydrolyzable covalent bond formed with a hydroxyl, $CO_2H$, amino, mercapto, or enolizable carbonyl moiety of the active ingredient to produce an ester, carboxylic acid, anhydride, amide, thioester, or enol ester, said linker being covalently bonded to a portion of subunits of a crosslinked polymer through a linker-polymer covalent bond selected from the group consisting of a nitrogen-carbon bond and a phosphorus-carbon bond.

2. The delivery system of claim 1 wherein the crosslinked polymer is selected from the group consisting of poly[(4-dialkylaminomethyl)styrene], poly[(3-dialkylaminomethyl)styrene], and mixtures of poly[(4-dialkylaminomethyl)styrene and poly(3-dialkylaminomethyl)styrene].

3. The delivery system of claim 2 wherein the crosslinked polymer is poly[(4-dimethylaminomethyl)styrene], poly[(3-dimethylaminomethyl)styrene], or a mixture thereof.

4. The delivery system of claim 3 wherein substantially all styrenic subunits of the crosslinked polystyrene polymer not bonded to the linker are substituted by quaternary ammonium salt moieties.

5. The delivery system of claim 4 wherein the active ingredient and the linker form a substituent on a 4-dimethylaminomethyl moiety or a 3-dimethylaminomethyl moiety having a structure represented by

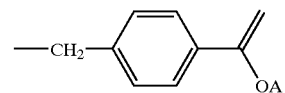

wherein OA is the covalently bonded active ingredient.

6. The delivery system of claim 4 wherein the active ingredient and the linker form a substituent on a 4-dimethylaminomethyl moiety or a 3-dimethylaminomethyl moiety having a structure represented by:

wherein

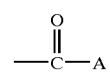

is the covalently bonded active ingredient.

* * * * *